United States Patent [19]

Buchalter

[11] 4,002,221

[45] Jan. 11, 1977

[54] METHOD OF TRANSMITTING ULTRASONIC IMPULSES TO SURFACE USING TRANSDUCER COUPLING AGENT

[76] Inventor: Gilbert Buchalter, 555 Mount Prospect Ave., Newark, N.J. 07104

[22] Filed: Nov. 15, 1974

[21] Appl. No.: 524,316

Related U.S. Application Data

[60] Continuation-in-part of Ser. No. 304,713, Nov. 18, 1972, abandoned, which is a continuation-in-part of Ser. No. 76,610, Sept. 29, 1970, abandoned, which is a division of Ser. No. 290,402, Sept. 19, 1972.

[52] U.S. Cl. .............................. 181/.5; 73/71.5 US; 128/2 V; 128/2.06 E; 128/24 A; 128/417; 128/419 D; 128/419 S; 181/402; 252/316; 252/500; 252/518
[51] Int. Cl.[2] ........................................ G10K 11/00
[58] Field of Search ........... 128/417; 252/316, 500, 252/518; 106/169, 170; 73/71.5 US; 204/157.1 S; 181/402, .5

[56] References Cited

UNITED STATES PATENTS

| 3,134,720 | 5/1964 | Green et al. ................... 252/316 X |
| 3,427,382 | 2/1969 | Haefele ......................... 252/316 X |
| 3,499,844 | 3/1970 | Kibbel, Jr. et al. ................ 252/316 |
| 3,567,657 | 3/1971 | Lichtenstein ..................... 252/500 |
| 3,826,127 | 7/1974 | Molina ..................... 73/71.5 US X |

*Primary Examiner*—Richard D. Lovering
*Attorney, Agent, or Firm*—Hopgood, Calimafde, Kalil, Blaustein and Lieberman

[57] ABSTRACT

Gel compositions are disclosed containing a primary thickening agent (e.g. carboxy polymethylene polymer) combined with small but effective amounts of an auxiliary hydroxy-containing thickener, e.g. an hydroxy alkyl cellulose polymer. The gel is particularly suitable for use with transducers wherein the gel is introduced between a transducer element (for example, an electrode) and skin or surface. The gel compositions are advantageous in that they do not irritate the skin, do not corrode the transducer element, are slow to dry and do not substantially leak out from the area of contact. The process of using the gel is also included.

3 Claims, No Drawings

METHOD OF TRANSMITTING ULTRASONIC IMPULSES TO SURFACE USING TRANSDUCER COUPLING AGENT

This application is a continuation-in-part of Ser. No. 304,713, filed Nov. 18, 1972 and now abandoned, which is a continuation-in-part of Ser. No. 76,610, filed Sept. 29, 1970 and now abandoned, and a divisional thereof Ser. No. 290,402 filed on Sept. 19, 1972.

BACKGROUND OF THE INVENTION

The application of electrical and ultrasonic energy in the form of impulses to stimulate or monitor the progress of medical therapy or physical rehabilitation are old and well known techniques. Basically, these techniques rely on the use of at least one transducer means applied to a surface, such as electrodes for applying electrical impulses and a sound transducer for applying ultrasonic impulses.

The surface to which the transducer may be applied may be the skin of an animal or human or the transducer element may be applied to the surface of an article for non-destructive testing purposes.

In the application of electrical impulses to the skin of an animal or person, the amperage which is applied is varying quantities can produce considerable differences in the muscular action generated by the electrical current. Since the skin has some resistance, the currents generated by the electrodes may irritate the skin. Generally, it is necessary to use a covering on the electrode, particularly if the galvanic action is intended for the deeper tissues. It is now accepted practice that unless a definite type of action is desired from a bare metal electrode, such as an electrolysis or metallic ionization, a galvanic current should preferably be applied with covered electrodes. This avoids the very painful irritation and burns which usually result, even when a moderately intense current is employed with bare electrodes.

Where electrical currents are used medically for various therapuetic applications, it is preferred that bare metal electrodes not be used on the surface of the body. For example, it has been observed that when such electrodes have been used, electrolytic decomposition occurs under the metal. Moreover, there is a considerable risk of burning due to the presence of acid or caustic or by electrical action.

If it is essential that low-tension currents be used, then the metal electrodes are conventionally covered with gauze or other adsorbent material in sufficient width to overlap the edges of the metal. These pads are used for galvanic faradicsinusoidal treatments. The pad on these electrodes is usually soaked with a saline solution which serves to soften the skin and ease the current. It also diffuses the electrolytic decomposition products and tends to prevent chemical burns. The burns caused by improper contact with too thinly coated metal electrodes or bare metal electrodes can be quite severe, resulting in blisters which in turn lead to secondary infection which heals slowly and which can be very painful.

One of the more important area which is amenable to treatment by the use of electrical stimulation is that involving denervated muscle. The stimulation retards the progression of atrophy. Usually, it may be necessary to have several stimulation sessions a day to retard the atrophy.

This desirably would be facilitated if the electrodes stay in contact with the afflicted area for a long period of time without constant removal or reimplacement. Even those electrode contact media which are presently commercially available do not permit the use of bare electrodes. They must be used in combination with gauze covering of the electrode. Furthermore, the gels which are commercially available have the disadvantage of tending to liquify under the influence of the ingredients in human perspiration, such as body salts.

Applications in which burned skin is a particular problem using prior art techniques is in electro-shock therapy and in the defribilation of hearts.

In summary, the areas of use may include electrical monitoring of the heart (for example, EKG), physiological stimulation and the like. The application of ultrasonic impulses may similarly be used for stimulation or as a diagnostic tool in non-destructive testing.

BRIEF SUMMARY OF THE INVENTION

Stating it broadly, the invention resides in the formulation of clear sparkling gels having a viscosity similar to mayonaise and which are suitable for use for a variety of applications, with particular use as transducer gels.

The novel gels of the invention do not degrade on the skin and resist the tendency to liquify due to perspiration. Moreover, the gel compositions of the invention permit the use of bare metal electrodes or transducers for a wide variety of electrical and/or ultrasonic uses. No other gels known to the art permit the use of bare electrodes for such purposes. It is customary in the art to use covered electrodes or transducers.

DETAILED DESCRIPTION WITH PREFERRED EMBODIMENTS

The gel compositions of this invention exhibit outstanding properties, the novel gel of the invention residing in the use of a particular combination of thickening agents in proper proportions which results in a gel which is resistant to body perspiration and which has a broad range of uses in electrical and ultrasonic applications.

In general, the major or primary constituent of the combination of thickeners is alkali metal salts of long chain ionic organic polymers. These thickeners are water soluble and have outstanding gel properties. Examples of polymeric thickeners include those selected from the group consisting of a copolymer of methyl vinyl ether and maleic acid, and corboxy polymethylene polymer.

The aforementioned copolymer thickener is available under the trademark GANTREZ sold by General Analine and Film Company (GAF) of New York, N.Y. The carboxymethylene polymer is available under the trademark "Carbopol" sold by the B. F. Goodrich Chemical Company.

The auxiliary thickener is any of a class in which there is a marginally water-soluble polymer with a long chain cellulosic backbone having at least one primary hydroxy group attached to each repeating cellulose molecule. These are non-ionic polymers. Generally, the auxiliary thickening polymers have a Brookfield viscosity at a 1 wt.% solution viscosity (25% C. with Spindle No. 4) of from 100 to 10,000, preferably 250 to 5,000 and most preferably 1,000 to 4,000. As examples, are included hydroxy methyl cellulose, hydroxy ethyl cellulose and hydroxy propyl cellulose, among others. The length of the aklyl group is not significant and usually ranges from 1 to 10 carbon atoms, preferably 1 to 7 and most preferably 1 to 5. However, it is preferred that the thickener used have no metallic cation constituent.

The especially preferred gels of this invention which exhibit outstanding electrode gel properties consist of a thickener combination of the primary thickener carboxy polymethylene polymer and the auxiliary thickener hydroxy ethyl cellulose polymer used in combination as a thickener with a water-glycol mixture.

Generally, the concentration of the primary thickener in the gel is about 1/20th of 1% to 10%, preferably ¼ or 1% to 5% and most preferably 0.80% to 3.5%. (Unless otherwise indicated, all weights in this application are weight percents).

The concentration of the auxiliary thickening agent in the gel formulation is generally from 1/1000 of 1% to 3%, preferably 1/100 of 1% to 1% and most preferably about 1/20 of 1% to ⅓ of 1%.

It is preferred that the auxiliary thickening agent have the highest molecular weight possible without being completely insoluble in a thickened water-glycol mixture.

The pH of the gel will range from between 3½ to 11½, preferably 5 to 9½, and most preferably 6 to 7.5. As a general rule of thumb, the pH of the gel composition, if it is to be used as an electrode gel, will be adjusted to be as close to the pH of the human skin as possible.

In general, the primary thickening agent component of the invention will have a molecular weight (Staudinger) of from 30,000 to 2,000,000, preferably 60,000 to 500,000 and even more preferably 100,000 to 300,000. It is somewhat difficult to establish an absolute value for an upper limit of the degree of polymerization above which the thickening agents no longer function as efficient thickeners.

The fact is that practical considerations appear to be a primary determining factor as to the major thickener polymers and their molecular weights which can be used for the purpose of the invention. Generally speaking, the higher the molecular weight of the primary or major thickener polymeric material, the more preferred it is for the purpose of thickening. But this is to be treated in consideration of the other factor that polar groups must also be present in the polymer to allow it to be useable in water gels. Since the water solubility of a polymer generally decreases when the molecular weight increases, one would think that this would not be a desirable property.

Nevertheless, the primary thickener polymers of the invention are really members of the broad class of polyelectrolyte polymers. These do not lose water solubility as their molecular weight increases unless they become crosslinked.

It is very difficult to determine the molecular weights of very high molecular weight polymeric compounds. The figures obtained will generally vary widely depending upon the method used to determine them. It is widely recognized, for example, that molecular weights for polymeric materials which have been furnished by manufacturers usually constitute an average of the molecular weights of the molecules present.

Among the various methods used to measure molecular weights of polymeric compounds there can be included osmometrig n-group, cryoscopic, ebullioscopic, light scattering, specific viscosity, intrinsic viscosity and ultra centrifuge. Each of these methods is in various degrees of development and each one has special type of polymeric compounds to which it is especially adapted.

Viscosity is a property which is much more frequently used by th polymer chemist as characterizing polymeric compounds than are molecular weights. This is no doubt due to the comparatively easier and less complicated methods for obtaining viscosity data. There is a recognized correlation between the viscosity of polymeric compounds and their relative molecular weights and, since such figures can be more meaningful and can frequently be more available than molecular weights, the polymeric thickeners described in this invention are characterized in terms of viscosity where possible. Thus, the viscosities of the primary thickening agents which can be used in the invention vary from a Brookfield Viscosity (CPS -centipoises per second) (20 rpm) of approximately 1000 to 100,000 at 1 wt.% aqueous concentration, preferably 15,000 to 90,000 and most preferably 18,000 to 80,000.

These viscosities are given terms of polymeric thickeners which have been neutralized to a pH of 7.

A particularly preferred major thickening agent is a series of thickeners of water-soluble resins sold by the B. F. Goodrich Chemical Company under the trademark of "Carbopol." This is a carboxy vinyl polymer, i.e. carboxy polymethylene which is essentially a vinyl polymer with active carboxylic groups. It is highly ionic and slightly acidic. Any one of the Carbopol series, such as 934, 940 and 941, can be used.

The particularly preferred auxiliary thickener is hydroxy ethyl cellulose. This is obtainable under the trade name "Cellosize" from the Union Carbide Company.

Another inventive feature of the gel, particularly the preferred gel compositions of the present invention, involves the use of the particular humectant. The humectants are preferably alkylene glycols wherein the alkylene group comprises from 2 to 10 carbon atoms, preferably from 2 to 5 carbon atoms. Propylene glycol is conventionally an electrode gel component. In the electrode gels of the present invention, a slight excess of propylene glycol is employed and in turn the normal preservative ingredients methyl paraben and propyl paraben have preferably been omitted.

Generally from 10 to 25, preferably 14 to 20 and most preferably 16 to 18.5 wt.% of humectant component is included in the composition.

Not only does the use of extra glycol result in the distinct advantage of eliminating a more allergenic component but it also results in the additional advantage that perfumes need not be added to the gel product. This is because the conventionally used methyl and propyl components are unpleasant and must be masked with a perfume.

Thus, the propylene glycol ingredient serves manifold purposes. It is a humectant and, therefore, it retards drying time. It permits the elimination of auxiliary preservatives and it is also a wetting or solubilizing agent due to its polyhydric alcohol characteristics.

This permits extraordinarily good wetting, solubilizing and penetrating effect when used on the skin. Therefore, as a consequence, whatever oil-innerface barriers are set up between the electrode and the skin, a composition such as propylene glycol tends to lower the total electrical resistance because of its ability to wet, solubilize and penetrate the innerface. Water is added to make up the balance of the composition. Low molecular weight monohydric alcohols are not generally desirable because they tend to evaporate too rapidly. But they can be used in minor proportions to replace a part of the water.

Of course, as mentioned above, the mono-, bi-, and tri- valent salts are progressively bad actors in human perspiration in that they are known to cause degradation of electrode gels. This results in a liquification phenomenon which caused conventional gels to thin out and become somewhat ineffective. The use of the auxiliary thickening agents is effective in preventing this liquification.

Generally speaking, the preparation of the gel involves the dispersion of all the thickening and humectant ingredients of the gel as well as the trace ingredients such as dye in about half the total water which is needed.

All the ingredients are then dispersed with high speed mixing using a mixer such as the Lightning line of mixers obtainable from the Mixing Equipment Corp. It is possible to use moderate speed mixing but that is less preferable because it is less efficient. Subsequently, the balance of the water is added less any water which is needed for the neutralizing agent. The mixture is allowed to stabilize and an alkaline solution is added to the mixture slowly. The pH is adjusted as described above.

Alkaline agents, such as alkali metal hydroxides and certain organic amines may be used to neutralize the primary thickening component of the inventive composition. Sodium and potassium hydroxides are preferred, potassium hydroxide being particularly preferred in that it imparts improved electrode properties to the resultant gel compositions, for example improved conductivity.

A particularly preferred composition is one containing potassium because potassium conducts electricity better. Where very high concentrations of alkali metal ions are desired for exceptional conductivity, about 3 wt.% Carbopol is used and it is supplemented with potassium citrate or sodium citrate and with citric acid as a buffer.

Alkali metal citrate may be optionally employed in amounts up to 5%, e.g. about 0.5 to 5%, preferably 0.8 to 3 wt.% of the composition. Similarly, citric acid may be optionally employed up to about 5 wt.% or in the same proportions as above. The term "up to" means with or without the addition of these compounds. Other buffering acids such as benzoic, salicyclic, tartaric, malic, lactic and the like can be used in place of the citric acid. These are weak organic acids.

It will be noted in the foregoing general description that no inorganic salts are added to the gel composition. In many of the gels which are known to the prior art, an inorganic salt is a common ingredient for the purposes of electrical conduction. Salt is apparently the primary cause of skin irritation. It is theorized that this is brought about by the electrode corrosion products which result from the action of the salt on the metallic electrode.

The gel of the invention has a low polarization potential. Indeed, in actual use, it appears to be essentially non-polarizing.

The preferred product of the invention having a careful balance of primary thickening agent, auxiliary thickening agent and humectant has a unique penetrating action which gives it a total lower electrical resistance between the skin, the gel and the electrode as compared to competitive products.

The gel composition of the invention can be used for long term monitoring where intensive care is needed such as in a situation where electrodes are placed on the patient and may remain for many hours, even weeks.

As illustrative of the various embodiments of the invention, the following examples are given.

EXAMPLE 1

A composition of the prior art and a preferred composition of the present invention having the following formulations were prepared for comparison purposes. (All percentages are weight percents unless otherwise indicated).

|  | Most Related Commercial Material | Composition of the Present Invention |
|---|---|---|
| Carboxy Polymethylene (Carbopol 934) (1) | .6% | 3% |
| Hydroxy Ethyl Cellulose (QP 100M) (2) | — | 1/8 of 1% |
| Propylene Glycol | 16% | 18% |
| Methyl Paraben | .18% | — |
| Propyl Paraben | .03% | — |
| Perfume | .004% | — |
| F.D. & C. Color | .001% | .001% |
| Sodium Hydroxide | 39% (Based on Carbopol) | — |
| Potassium Hydroxide | — | 2.5% |
| Potassium Citrate | — | 3% |
| Citric Acid | — | 1% |
| Water | Balance to 100% | |

(1) This is a white powder which has a Brookfield RVF or RVJ 20 rpm No. spindle at 25° C. ± 0.5° C. for an 0.2% neutralized solution of from 2,050 to 5,450.
(2) obtainable as Cellosize HEC from Union Carbide
QP = Quick Processing. A non-ionic water-soluble cellulose ether with a solution viscosity at 1 wt.% in H$_2$O of 2,500 to 3,000 CPS. This is Brookfield Viscosity at 25° C. with Spindle No. 4.

The above described commercial material was prepared as follows:

The preservatives (methyl and propyl paraben) were dissolved in the propylene glycol. The perfume was then dispersed. One half of the total volume of the water was then added. Carbopol 934 was dispersed with high speed mixing. The dye was then added. The balance of the water was added, less the water needed for dissolving the alkali metal hydroxide.

The composition of the invention was similarly formulated except that citric acid and potassium citrate were preferably added prior to the addition of Carbopol and the hydroxy ethyl cellulose being added either simultaneously with the Carbopol or after the Carbopol.

The total mixture was allowed to stand, without further agitation, for several days for the air bubbles to disperse. Upon completion of this stabilizing time, the alkali metal hydroxide was dissolved in the proper amount of water and added to the above mixture with slow agitation until the gel was formed and was mixed until completely uniform.

The mixture prior to neutralization with alkali metal hydroxide was characterized by being thin, pourable, milky liquid with approximately the viscosity of light cream. The physical characteristics upon completion of neutralization was a clear, sparkling gel with a viscosity similar to that of mayonnaise or sour cream. That is to say, the product would not pour or run unless it was under pressure (squeezed out of a plastic container).

The major differences in the formulation of the gel composition of the invention in contrast to the prior art gel are:

The methyl and propyl paraben could be eliminated as research indicated that increased percentage of propylene glycol in itself was sufficient for preservation. However, with lower amounts of propylene glycol, these preservatives may be used.

The hydroxy ethyl cellulose (HEC) was dispersed simultaneously with the Carbopol 934. This resulted in a thicker or higher viscosity preneutralized liquid as the thickening ability of HEC is not dependent upon pH.

Neutralization was effected with potassium hydroxide as the alkaline agent in contrast to sodium hydroxide as the potassium ion is a better electrical conductor than sodium (it is, however, a poorer ultrasound conductor).

The eliminaion of the methyl and propyl paraben as preservatives enabled the production of an ordorless product which did not require the necessity of perfume to mask the preservative odor. The propylene glycol content of the novel gel composition is higher than that of the prior art gel because in the novel gel composition, it is used for three different and distinct purposes. In the prior art gel, it is used solely as a humectant for retarding drying time.

While it is used in the novel gel composition for the same purpose, a higher concentration is used so that the drying time can be prolonged. This higher concentration enables it to be used as a preservative in the composition. It also has the advantage of being a wetting or solubilizing agent due to the fact that it is an alcohol.

This wetting, solubilizing and penetrating effect is responsible for lowering the total electrical resistance when in use, as it tends to wet, solubilize and penetrate the oil-skin barrier.

Another example of a composition for particular use as an ultrasonic gel is one containing approximately ½ of 1 wt.% carboxy polymethylene polymer, approximately ¼ of 1 wt.% hydroxy ethyl cellulose, approximately 18 wt. % propylene glycol and an amount of sodium hydroxide calculated at 40% of the amount of carboxy polymethylene polymer present. Where the composition is used for transmitting electrical impulses, it is preferred that potassium hydroxide be used in place of sodium hydroxide in an amount 55% by weight of the carboxy polymethylene polymer present.

A preferred gel composition for transmitting electrical impulses is one containing approximately 3 wt.% carboxy polymethylene polymer, approximately ⅛ of 1 wt. % hydroxy ethyl cellulose, approximately 18% propylene glycol, approximately 2.5 wt.% potassium hydroxide based on the total composition, approximately 3 wt.% potassium citrate and approximately 1 wt.% citric acid.

EXAMPLE II

Tests were performed which have proven that using the novel gel composition for regular electrocardiogram monitoring allows the use of either a pediatric electrode, or a specially modified electrode (original tests were done using a penny and a lightweight shielded cable instead of the cumbersome and costly suction cup chest electrodes and the strap electrodes for the arm or leg).

The high viscosity of the novel gel composition held the small electrode (pediatric or penny) in place without the necessity of mechanical assistance from the suction cup or straps resulting in a saving time and cost.

EXAMPLE III

The basic technique for stimulation of denervated muscles with direct current was used. The dispersive pad electrode was thoroughly saturated with warm water and placed outside the area being treated — in all cases the hand on the affected side was used to complete the circuit.

The felt and asbestos covering was removed from a conventional "diagnostic" tap key electrode. The stainless steel electrode plate used was 2 cm. in diameter. The dispersive electrode was left intact with its commercial covering over the plate. A single sheet of paper toweling cut to size was used over the dispersive pad as a sanitary measure.

The electrode gel composition of the invention described in Example I was applied to the active electrode and to the motor point areas with a 0.5 cm. thick glob. A direct current was used for stimulation — interrupted by means of a make and break technique with the tap key electrode. Care was taken to apply minimal pressure on the tap key electrode. Too much pressure on the electrode caused a mechanical removal of the gel, resulting in patient discomfort and diminished response.

Following completion of the treatment, the gel was removed from the skin with a tissue. The active electrode was rinsed under hot water and placed in a cold sterilization pan.

A group of five volunteers was used to determine the comfort level as well as skin sensitivity to the technique employed. The motor points of the face were used as the testing site due to the inherent sensitivity of the face. A conventional electrode was also used with the usually recommended media on the volunteer subjects to provide a basis for comparison of intensity required for good muscle contractions.

Following the trial period with the volunteer subjects, five patients, one male and four female, ranging in age from forty-four to sixty-five were treated with the new technique outlined. Pathologies included: Bell's Palsy 3; Ramsay Hart Syndrome; Diabetic neuropathy.

A total of one-hundred thirty-two treatments was given. Frequency of treatment ranged from once daily to once weekly. Four of the five patients received electrical stimulation to the face. The fifth patient, a female, received stimulation to the anterior tibialis for treatment of a diabetic neuropathy. All muscles stimulated were denervated by the course of the specific pathologies.

The use of the aqueous gel composition of the invention facilitated placement and permitted a sliding movement of the electrode on the skin; thus, minute relocations of the electrode were possible without losing skin contact while the optimal response point was being determined.

The viscosity of the gel provided constant contact even over hairy areas and structural contours which are usually problem areas. This continuous rather than interrupted contact of the electrode provided a new level of patient comfort. Patient comfort level was also improved through the reduction of intensity and local sensation of heat. The cool skin sensation experienced by the patient diminishes his anxiety regarding burn.

The use of a sanitary covering, such as gauze, paper and the like over the conventional electrodes, is, at best, a false security. Since water or media solution necessarily passes through these "sanitary" coverings which are not bacterial filters, the bacteria have a free avenue of flow from the electrode covering to the patient. This potential hazard of cross infection can be eliminated by using the bare electrode as described. The bare electrode, which can be sterilized, has no areas for bacteria to collect, grow and cause cross contamination. Further, there is no time lost wrapping the electrodes as a "protective" measure.

Basically, the use of the gel composition of the invention provides an entirely new process technique to the art for electrical stimulation using bare electrodes.

Thus, for the first time with galvanic currents, it was possible to obtain good muscle contractions with low intensity current electrode sterilization was readily obtainable, good skin contact was facilitated and cutaneous hyperemia and erythemia were absent.

The tests described for Examples II and III were based on the composition of the invention described in Example I. In this connection, a preferred composition range is one containing about 1/10 of 1 wt.% to 3 wt.% of carboxy polymethylene polymer, about 1/10 of 1 wt.% to 3 wt.% hydroxy ethyl cellulose, and about 14% to 22 wt.% propylene glycol, the alkaline agent employed being selected from the group consisting of sodium hydroxide and potassium hydroxide. As special additives, this composition may optionally contain 0.8% to 3 wt.% alkali metal citrate and 0.8% to 3 wt.% citric acid.

Although the present invention has been described in conjunction with preferred embodiments, it is to be understood that modifications and variations may be resorted to without departing from the spirit and scope of the invention as those skilled in the art will readily understand. Such modifications and variations are considered to be within the purview and scope of the invention and the appended claims.

What is claimed is:

1. In a method of transmitting ultrasonic impulses to a surface in contact with transducer means with a conductivity gap therebetween, the improvement comprising applying a transducer coupling agent to said conductivity gap formed of a composition consisting essentially of:

about 1/20th of 1 wt% to 10 wt% of a long chain water soluble ionic polymeric thickener having a Brookfield Viscosity (CPS) of approximately 1000 to 100,000 at 1 wt% concentration in $H_2O$ and neutralized with an alkaline agent, said thickener being selected from the group consisting of a co-polymer of methyl vinyl ether and maleic anhydride, carboxy polymethylene polymer and mixtures thereof, about 1/1000 of 1 wt% to 3 wt% of a hydroxy alkyl cellulose polymer as an auxiliary thickener, about 10% to 25% by weight of a polyalkylene glycol humectant, said alkylene group containing 2 to 10 carbon atoms, up to about 5 wt% of an alkali metal salt of a weak organic acid, up to about 5 wt% of a weak organic acid, and the balance essentially water, said gel having a pH of about 3.5 to 11.5.

2. In a method of transmitting ultrasonic impulses to a surface in contact with transducer means with a conductivity gap therebetween, the improvement comprising applying to a transducer coupling agent to said conductivity gap formed of a composition consisting essentially of:

about 1/10 of 1 wt% of 3 wt% of carboxy polymethylene polymer substantially neutralized with an alkaline agent, about 1/10th of 1 wt% to 3 wt% of hydroxy ethyl cellulose, about 14% to 22% by weight of propylene glycol, and the balance essentially water, said gel having a pH of about 5 to 9.5--.

3. The method of claim 2 wherein said energy in pulses is ultrasonic vibrations and wherein said gel composition contains approximately 1/2 of 1 wt% carboxy polymethylene polymer, approximately 1/4 of 1 wt% hydroxy ethyl cellulose, approximately 18 wt% propylene glycol and approximately 40 wt% of sodium hydroxide based on the amount of carboxy methylene polymer present.

* * * * *

UNITED STATES PATENT OFFICE
CERTIFICATE OF CORRECTION

Patent No. 4,002,221                   Dated January 11, 1977

Inventor(s) Gilbert Buchalter

It is certified that error appears in the above-identified patent and that said Letters Patent are hereby corrected as shown below:

Column 10, line 34, after "applying" delete "to"

Column 10, line 37, after wt% "of" should read -- to --.

Signed and Sealed this

Thirty-first Day of May 1977

[SEAL]

Attest:

RUTH C. MASON  
Attesting Officer

C. MARSHALL DANN  
Commissioner of Patents and Trademarks